US00PP09663P

United States Patent [19]

Klinger, Jr.

[11] Patent Number: Plant 9,663

[45] Date of Patent: Oct. 15, 1996

[54] SYNGONIUM 'BETH'

[75] Inventor: Paul E. Klinger, Jr., Lake Mary, Fla.

[73] Assignee: Garden Arts Nursery, Inc., Longwood, Fla.

[21] Appl. No.: 391,371

[22] Filed: Jan. 18, 1995

[51] Int. Cl.[6] ..... A01H 5/00

[52] U.S. Cl. ..... Plt./88.1

[58] Field of Search ..... Plt./88.1

[56] References Cited

U.S. PATENT DOCUMENTS

P.P. 5,807 11/1986 Kallert ..... Plt./88.1
P.P. 6,120 3/1988 Welter ..... Plt./88.1

OTHER PUBLICATIONS

Chase, A. R. (1994) "Are Your Syngoniums Resistant to Disease?" *Foliage Digest* vol. 17, No. 10, Oct., pp. 1–3.

*Primary Examiner*—James R. Feyrer
*Attorney, Agent, or Firm*—Arthur G. Yeager

[57] ABSTRACT

A new cultivar of Syngonium characterized by attractive and variegated foliage having prominent light interveinal areas in vivid contrast and divided by small darker veins. The petiole color is light brown and accents the leaf coloration. The freely suckering habit provides a growth which is compact and full in appearance. The new cultivar has genetic resistance to the bacterial disease caused by *Xanthomonas campestris* p.v. '*diffenbachiae*'.

2 Drawing Sheets

BACKGROUND OF THE NEW PLANT

The present invention relates to a new cultivar of Syngonium which was discovered in 1990 as a self pollinated seedling of *Syngonium podophyllum* "White Butterfly". The plant described herein is possessed of exceptional color and appearance, and has been asexually propagated under the applicant's direction for the past 3½ years in a nursery at Longwood, Fla. Repeated propagations by node cutting for many generations have demonstrated the stability of the genetic characteristics of this new cultivar.

BRIEF DESCRIPTION OF THE DRAWING

Comprehension of the color and other visual aspects of the inventive plant is facilitated by reading the following description in conjunction with the annexed color photograph in which.

DESCRIPTION OF THE NEW PLANT

Figure 1:
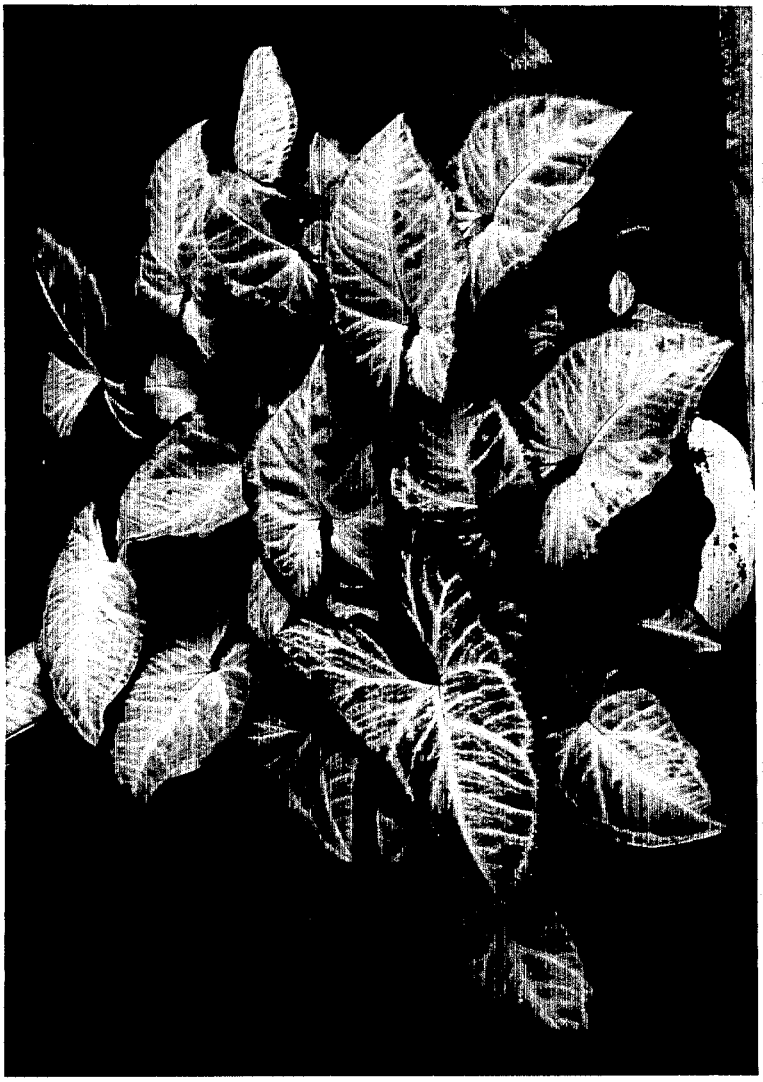
FIG. 1 is a color photograph of a top perspective view of the novel Syngonium plant of the present invention.
Figure 2:
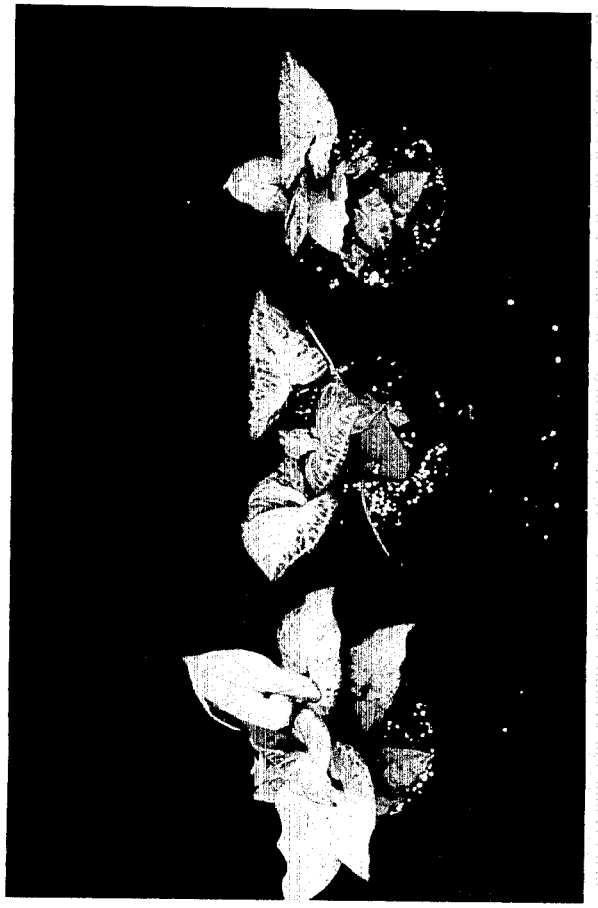
FIG. 2, shows specimens of the plant 'Beth' of this disclosure, on the left also identified as 'No. 9'; the parent plant 'White Butterfly' in the middle; and, a sibling seedling identified as 'No. 2', which shows some resistance to *Xanthomonas campestris,* p.v. *dieffenbachiae,* on the right.

Origin: Seedling from 'White Butterfly'.

Parentage: *Syngonium podophyllum* 'White Butterfly'.

Classification: *Syngonium podophyllum* cultivar Beth.

Form: Erect, compact growth type with free suckering habit to provide full appearance to the plant.

Growth rate: Good. Equal to or better than parent variety 'White Butterfly'.

Propagation: Asexual reproduction either by tissue culture or cuttings.

Plant: In a 15 cm standard pot, after approximately 24 weeks of growth under appropriate conditions beginning with a 10-week-old rooted liner obtained from tissue culture, the canopy top of Beth will be approximately 25 cm from the soil surface and 32 cm wide. Plant height, with the leaves held upward, will be approximately 30 cm. An average number of 8 basal shoots will be produced per plant. Size of mature leaves will average 7 cm wide and 12 cm long. The ultimate size of Beth if planted in a very large container and grown under appropriate conditions, is unknown. The plant Beth is comparable and is intended to be generally indistinguishable from 'White Butterfly' grown under the same conditions.

Stem: The stem color is 148 A/B but it is generally not visible because of the clasping nature of the petiole wings, but these do not entirely cover the stem.

Petiole: The petiole color is 197A at the base and gradually changes to 146A as it approaches the leaf blade.

Leaf:

*New.*—The primary veins and the interveinal areas are color 145C in the areas adjacent to the veins and gradually darkens to 145A in remote areas. The secondary veins are color 139A. The undersurface of the leaf is uniformly color 147B.

*Mature.*—The interveinal areas of older leaves are color 144 A/B while the veins and leaf margins are a darker color 139A. The area of darker coloration is more pronounced near the leaf margins. The undersurface is a uniform color 147B.

NOTE: All color references are measured against The Royal Horticultural Society Colour Chart. Colors are approximate as color depends on horticultural practices such as light level and fertilization rate, among other varying parameters.

The above plant description distinguishes itself from its antecedents and known related varieties by a growth habit which provides specimens with the repeated observed and tested traits and basic characteristics of the K94-1 cultivar from other Syngonium of the same general type such as Syngonium 'White Butterfly' or any other of those described by Bailey, L. H. and E. Z., 1976, *Hortus Third,* Macmillan, New York; Graf, A. B., 1978. *Tropica—Color Cyclopedia of Exotic Plants and Trees.* Roehrs Co., East Rutherford, N.J.; or Henley, R. W. and C. A. Robinson. 1993. Nephthytis cultivars to know and grow. *Proc. Fla. State Hort. Soc.* 106:343–347.

A new and distinct variety of Syngonium is shown and described above and is characterized by:

A. Attractive variegated foliage consisting of lighter interveinal areas separated by small darker leaf veins;

B. Petiole color is light brown and accents the leaf coloration;

C. Freely suckering habit gives the plant a compact and full appearance; and

D. The plant has genetic resistance to the bacterial disease caused by *Xanthomonas campestris* p.v. '*diffenbachiae*', as shown by the Chase report incorporated herein by reference.

This report entitled Resistance of Syngoniums to Xanthomonas blight was conducted by A. R. Chase of Chase Research Gardens, and sent to the inventor on May 25, 1994. The Syngonium Named 'K94-1' is the 'Line #9' referred to throughout this report (also Line 190 9 is designated as 'Beth').

Although the plant of this invention is described for its pheontypic expression when grown to market size under commercial conditions in a nursery in Longwood, Fla., it is to be understood that the expressions of this plant would be expected to vary when cultured under varying conditions in different locations.

What is claimed is:

1. A new and distinct variety of *Syngonium podophyllum plant*, as shown and described herein.

* * * * *

NO. 9 'BETH'

PARENT 'WHITE BUTTERFLY'

NO. 2 SIBLING